United States Patent [19]

Beck et al.

[11] 4,299,614
[45] Nov. 10, 1981

[54] NOVEL ALGICIDAL METHOD UTILIZING 1,4-DIPHENYL-3-PYRAZOLIN-5-ONES

[75] Inventors: James R. Beck; Robert P. Gajewski, both of Indianapolis, Ind.

[73] Assignee: Eli Lilly and Company, Indianapolis, Ind.

[21] Appl. No.: 160,796

[22] Filed: Jun. 19, 1980

[51] Int. Cl.$^3$ ............................................. A01N 43/56
[52] U.S. Cl. ........................................... 71/67; 71/92
[58] Field of Search ............................................. 71/67

[56] References Cited

U.S. PATENT DOCUMENTS

| | | | |
|---|---|---|---|
| 3,200,128 | 8/1965 | Wagner | 71/67 X |
| 4,075,003 | 2/1978 | Beck et al. | 71/92 |
| 4,084,955 | 4/1978 | Kornia et al. | 71/92 |
| 4,118,574 | 10/1978 | Beck et al. | 71/92 X |

OTHER PUBLICATIONS

Weed Research, 1975, vol. 15, pp. 401–406.
Chemical Abstract, *Tex. J. Sci.*, 1969, 20(4):329.

*Primary Examiner*—Catherine L. Mills
*Attorney, Agent, or Firm*—Gerald V. Dahling; Arthur R. Whale

[57] ABSTRACT

A class of 1,4-diphenyl-3-pyrazolin-5-ones are useful as aquatic algicides. The compounds have small alkyl substituents at the 2-position, and the phenyl rings may be substituted as well.

15 Claims, No Drawings

NOVEL ALGICIDAL METHOD UTILIZING 1,4-DIPHENYL-3-PYRAZOLIN-5-ONES

SUMMARY OF THE INVENTION

This invention provides to the algicidal chemical art compounds, covered generally by U.S. Pat. Nos. 4,118,574 and 4,075,003, of the formula

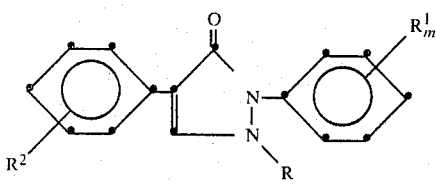

wherein

R represents $C_1$–$C_3$ alkyl;

$R^1$ and $R^2$ independently represent hydrogen, chloro, fluoro, bromo, methyl, methoxy, hydroxymethyl, or trifluoromethyl without restriction as to substituent or position except that when $R^1$ is para-chloro, m=1, and $R^2$ is simultaneously meta-trifluoromethyl, R is not simultaneously ethyl or propyl, and m=1 or 2 with the proviso that when m=2, each $R^1$ is halo.

The invention provides new algicidal compositions, and methods of reducing the vigor of unwanted algae, which make use of the compounds above.

The compounds of the present invention are readily prepared by a 3-step process. First, a methyl or ethyl ester of phenylacetic acid, bearing the $R^2$ substituent on the phenyl ring, is reacted with di(Alk) formamide di-(Alk) acetal neat or in dimethylformamide to produce an intermediate substituted ester of atropic acid of the formula (I) below.

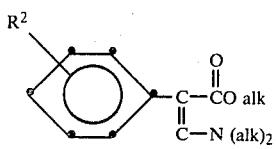

The term Alk refers to methyl or ethyl. The reaction is carried out at temperatures from about 80°–140° C. in a flask open to the atmosphere.

The intermediate I is then reacted with a phenylhydrazine or a hydrohalide thereof, bearing the $R^1$ substituent, if any, on its phenyl ring, to form the desired product, lacking the 2-alkyl group. The reaction is a known type of reaction, cf. U.S. Pat. Nos. 4,075,003 and 4,118,574. When a phenylhydrazine in the free base form is used, the reaction is carried out in an aprotic solvent. The aromatic solvents such as benzene and toluene, the aliphatics such as hexane and octane, and the halogenated solvents such as methylene chloride and chloroform are appropriate solvents. Xylenes are the preferred solvents. The most convenient reaction temperature is the reflux temperature of the reaction mixture, but other temperatures from room temperature to about 120° C. can be used if convenient in a given instance.

When a phenylhydrazine hydrohalide is used, the reaction can be carried out in an aprotic solvent as described above in the presence of a base. Tertiary organic amines such as triethylamine, pyridine, triethanolamine and the like, and inorganic bases such as potassium carbonate, sodium bicarbonate, alkali metal hydroxides and the like are satisfactory bases.

Alternatively, reactions using phenylhydrazine hydrohalides may be performed by first reacting the hydrazine with the intermediate I in a lower alkanol at the reflux temperature of the mixture to exchange the di-(Alk) amino group of I with the arylhydrazine moiety. The resulting intermediate may be cyclized by heating in an aprotic solvent such as xylene at temperatures from about 50°–120° C. Alternatively, the resulting intermediate may be cyclized by heating in a lower alkanol at reflux temperature with inorganic bases such as potassium carbonate, alkali metal hydroxides, or alkali metal alkoxides.

The 2-substituent is easily added by alkylation with, for example, an alkyl iodide in the presence of a strong inorganic base. It is also possible to alkylate at the 2-position with a dialkyl sulfate under strong basic conditions. Again, the most convenient temperature for the alkylation is the reflux temperature of the reaction mixture, as is commonly done in such reactions. Alkylations of this type are frequently performed and are common in the chemical literature.

All of the starting compounds used in synthesizing the pyrazolinones are commonly known in the chemical art and are readily obtainable.

A few typical preparative examples will be shown to assure that those skilled in the art can obtain any desired compound of this invention. All of the products described below were identified by nuclear magnetic resonance analysis and elemental microanalysis.

EXAMPLE 1

2-Methyl-1-phenyl-4-(α,α,α-trifluoro-3-tolyl)-3-pyrazolin-5-one

A 10.9 gram portion of 3-trifluoromethylphenylacetic acid, methyl ester was combined with 11.9 grams of dimethylformamide dimethyl acetal and the mixture was heated overnight on the steam bath. In the morning, the reaction mixture was taken up in methanol and poured over ice. The aqueous mixture was filtered, and the solids were recrystallized from aqueous ethanol to produce 4 grams of 3-trifluoromethyl-β-(dimethylamino)atropic acid, methyl ester, m.p. 45°–49° C.

The ester prepared above was combined with 1.6 grams of phenylhydrazine in 25 ml. benzene and the mixture was refluxed overnight. About 25 ml. para-xylene was added and the mixture was refluxed for 2 hours more. The reaction mixture was then cooled, and the resulting solids were separated by filtration and identified as 2.6 grams of 1-phenyl-4-(α,α,α-trifluoro-3-tolyl)-3-pyrazolin-5-one.

A 1.5 gram portion of the pyrazolinone was dissolved in 50 ml. methanol, and 0.7 grams methyl iodide and 0.7 grams potassium carbonate were added. The mixture was stirred at reflux temperature overnight. The mixture was then poured over ice, and the aqueous mixture was filtered to remove the product, which was recrystallized from ethyl acetate-hexane. The product was 0.85 grams 2-methyl-1-phenyl-4-(α,α,α-trifluoro-3-tolyl)-3-pyrazolin-5-one, m.p. 153°–155° C.

Calculated: C, 64.15; H, 4.12; N, 8.80; Found: C, 64.17; H, 4.19; N, 8.77.

EXAMPLE 2

2-Ethyl-1-phenyl-4-($\alpha,\alpha,\alpha$-trifluoro-3-tolyl)-3-pyrazolin-5-one

A 2.5 gram portion of the 2-unsubstituted pyrazolinone of Example 1 was reacted with 1.2 grams ethyl iodide. The alkylated product was 1.2 grams 2-ethyl-1-phenyl-4-($\alpha,\alpha,\alpha$-trifluoro-3-tolyl)-3-pyrazolin-5-one, m.p. 156°–157° C.

Calculated: C, 65.06; H, 4.55; N, 8.43; Found: C, 65.25; H, 4.65; N, 8.40.

EXAMPLE 3

1-(3-Chlorophenyl)-2-methyl-4-($\alpha,\alpha,\alpha$-trifluoro-3-tolyl)-3-pyrazolin-5-one A 3.5 gram portion of the atropic ester of Example 1 was reacted with 2.3 grams 3-chlorophenylhydrazine hydrochloride in the presence of 1.3 grams triethylamine in about 50 ml. meta-xylene. The mixture was then stirred at reflux overnight, and the reaction mixture evaporated to dryness under vacuum. The residue was partitioned between ethyl acetate and water, and the organic layer was dried over sodium sulfate and evaporated to dryness. The residue was chromatographed on silica gel with ethyl acetate as the eluant. The product containing fractions were combined and evaporated to dryness to produce a crude product, which was recrystallized from methanol to produce 2 grams 1-(3-chlorophenyl)-4-($\alpha,\alpha,\alpha$-trifluoro-3-tolyl)-3-pyrazolin-5-one, m.p. 182°–184° C.

A 1.65 gram portion of the above intermediate was alkylated with 2 grams methyl iodide to produce 1 gram of the desired product, m.p. 130°–131° C.

Calculated: C, 57.89; H, 3.43; N, 7.94; Found: C, 58.13; H, 3.59; N, 8.04.

EXAMPLE 4

1,4-Bis-($\alpha,\alpha,\alpha$-trifluoro-3-tolyl)-2-methyl-3-pyrazolin-5-one

A 3.5 gram portion of the atropic ester of Example 1 was reacted with 2.7 grams $\alpha,\alpha,\alpha$-trifluoro-3-tolylhydrazine hydrochloride in the presence of triethylamine to produce 2.4 grams 1,4-bis-($\alpha,\alpha,\alpha$-trifluoro-3-tolyl)-3-pyrazolin-5-one, m.p. 207°–208° C. A 1.8 gram portion of the above pyrazolinone was alkylated with 2 grams methyl iodide to produce 1.25 grams of the desired product, m.p. 110°–111° C.

Calculated: C, 56.26; H, 2.62; N, 7.29; Found: C, 56.04; H, 2.86; N, 7.19.

EXAMPLE 5

1-(3-Chlorophenyl)-2-ethyl-4-($\alpha,\alpha,\alpha$-trifluoro-3-tolyl)-3-pyrazolin-5-one A 2.6 gram portion of 1-(3-chlorophenyl)-4-($\alpha,\alpha,\alpha$-trifluoro-3-tolyl)-3-pyrazolin-5-one, prepared in Example 3, was alkylated with ethyl iodide to produce 0.25 grams of the desired product, an oily liquid.

Calculated: C, 58.95; H, 3.85; N, 7.64; Found: C, 58.89; H, 3.61; N, 7.52.

EXAMPLE 6

1,4-Bis-($\alpha,\alpha,\alpha$-trifluoro-3-tolyl)-2-ethyl-3-pyrazolin-5-one

A 4 gram portion of 1,4-bis-($\alpha,\alpha,\alpha$-trifluoro-3-tolyl)-3-pyrazolin-5-one (from Example 4) was heated with 20 ml. ethyl iodide, 3 grams potassium carbonate, and 40 ml. ethanol at reflux temperature for about 4 hours. The reaction product mixture was concentrated in vacuo and extracted with ethyl acetate. The extract was dried over anhydrous magnesium sulfate, the drying agent filtered off and the filtrate concentrated in vacuo. On standing overnight the residue solidified and was recrystallized from a mixture of hexane and benzene. The solid was chromatographed on a silica gel column using a mixture of ethyl acetate and hexane in the ratio of 1:2. The product from the column was then recrystallized from a mixture of hexane and benzene to yield the desired product, m.p. 110°–111° C.

Calculated: C, 57.00; H, 3.50; N, 7.00; Found: C, 56.63; H, 3.49; N, 6.85.

EXAMPLE 7

1-(3-Bromophenyl)-2-ethyl-4-($\alpha,\alpha,\alpha$-trifluoro-3-tolyl)-3-pyrazolin-5-one A 13.7 gram portion of the atropic ester of Example 1 was allowed to react with 11.2 grams 3-bromophenylhydrazine hydrochloride in 100 ml. methanol at reflux temperature overnight. The solvent was evaporated and the residue was refluxed in 100 ml. of metaxylene and 5 grams triethylamine for about 16 hours. The reaction mixture was concentrated in vacuo and the residue chromatographed on a silica gel column using 1:1 ethyl acetate-hexane. There was obtained 7.5 grams of product which was identified as 1-(3-bromophenyl)-4-($\alpha,\alpha,\alpha$-trifluoro-3-tolyl)-3-pyrazolin-5-one.

A 7.5 gram portion of the above pyrazolinone was combined with 4 grams potassium carbonate and 15 ml. ethyl iodide in 100 ml. ethanol and heated in the same manner as previously described for other similar compounds. There was obtained 2.0 grams of the desired product, m.p. approximately 106° C.

Calculated: C, 52.57; H, 3.43; N, 6.81; Found: C, 52.80; H, 3.49; N, 6.98.

EXAMPLE 8

2-Ethyl-1-(4-fluorophenyl)-4-($\alpha,\alpha,\alpha$-trifluoro-3-tolyl)-3-pyrazolin-5-one A 5.5 gram portion of the atropic ester of Example 1 was combined with 3.5 grams of 4-fluorophenylhydrazine hydrochloride and 2 grams triethylamine in 50 ml. benzene. The mixture was stirred at reflux temperature for 5 hours, after which about half of the benzene was allowed to evaporate and an equivalent amount of meta-xylene was added. The mixture was then stirred at reflux overnight, and the reaction mixture was evaporated to dryness under vacuum. The residue was partitioned between ethyl acetate and water, and the organic layer was dried over sodium sulfate and evaporated to dryness. The residue was chromatographed on silica gel with ethyl acetate as the eluant. The product containing fractions were combined and evaporated to dryness to produce about 3.5 grams of crude intermediate, which was recrystallized from methanol to produce 2.7 grams of purified 1-(4-fluorophenyl)-4-($\alpha,\alpha,\alpha$-trifluoro-3-tolyl)-3-pyrazolin-5-one, m.p. 171°–173° C.

A 6 gram portion of 1-(4-fluorophenyl)-4-($\alpha,\alpha,\alpha$-trifluoro-3-tolyl)-3-pyrazolin-5-one (prepared according to the teaching outlined above) was mixed with 4 grams potassium carbonate and 15 ml. ethyl iodide in 100 ml. ethanol and refluxed overnight. The desired product was isolated in the usual way, yield 1.8 grams, m.p. approximately 92° C.

Calculated: C, 61.72; H, 4.03; N, 8.00; Found: C, 61.87; H, 4.20; N, 8.06.

EXAMPLE 9

1,4-Bis-(3-chlorophenyl)-2-ethyl-3-pyrazolin-5-one

A 17 gram portion of 3-chlorophenylacetic acid, methyl ester, was combined with 12 grams dimethylformamide dimethyl acetal in 100 ml. dimethylformamide and the mixture was heated in an open flask at the boiling temperature of the mixture for 6 hours. The hot reaction mixture was then poured over ice, and the aqueous mixture was filtered. The solids were recrystallized from benzene/hexane to produce 13 grams of β-(dimethylamino)-3-chloroatropic acid, methyl ester, m.p. 84°–86° C. A 12 gram portion of the 3-chloroatropic acid, methyl ester was allowed to react with 10 grams of 3-chlorophenylhydrazine hydrochloride in 100 ml. of methanol at reflux temperature overnight. There was obtained 10 grams of product having a melting point of about 173°–174° C. and identified as 1,4-bis-(3-chlorophenyl)-3-pyrazolin-5-one.

A mixture of 7 grams of the pyrazolinone prepared above, 4 grams potassium carbonate, and 15 ml. ethyl iodide in ethanol was refluxed overnight. There was isolated, after recrystallization from ether, 3.0 grams of the desired product, m.p.=approximately 101° C.

Calculated: C, 61.28; H, 4.24; N, 8.41; Found: C, 61.04; H, 4.21; N, 8.55.

EXAMPLE 10

4-(3-Chlorophenyl)-2-ethyl-1-(α,α,α-trifluoro-3-tolyl)-3-pyrazolin-5-one

A mixture of 12 grams of the 3-chloroatropic acid, methyl ester (prepared in Example 9 above), 13 grams 3-(trifluoromethyl)phenylhydrazine hydrochloride and 100 ml. methanol was refluxed overnight to yield 4.6 grams of 4-(3-chlorophenyl)-1-(α,α,α-trifluoro-3-tolyl)-3-pyrazolin-5-one, m.p. 190°–192° C.

A mixture of 4.6 grams of the pyrazolinone prepared above, 4 grams potassium carbonate, 15 ml. ethyl iodide and 50 ml. ethanol was refluxed overnight. The reaction product mixture was worked up in the customary way to yield 1.8 grams of the desired product, m.p.=113°–114° C.

Calculated: C, 58.95; H, 3.85; N, 7.64; Found: C, 58.84; H, 3.89; N, 7.63.

EXAMPLE 11

1-(3-Chlorophenyl)-2-ethyl-4-phenyl-3-pyrazolin-5-one

A 120 gram portion of phenylacetic acid, methyl ester, was combined with 95 grams dimethylformamide dimethyl acetal in 200 ml. dimethylformamide, and heated to gentle reflux for about four days, while adding at intervals, 5 gram portions of dimethylformamide dimethyl acetal until a total of 140 grams additional had been added. At the end of the heating period, the reaction mixture was allowed to cool to room temperature and was poured over crushed ice. The oily product which separated eventually crystallized. The crystalline product was washed with water, cooled in a refrigerator, filtered off and air dried. The crude product was crystallized from cyclohexane to yield product having a melting point of about 58°–60° C., which was identified as β-(dimethylamino)atropic acid, methyl ester.

Calculated: C, 70.22; H, 7.37; N, 6.82; Found: C, 70.47; H, 7.36; N, 6.85.

A mixture of 10.5 grams of the atropic acid, methyl ester, 9.1 grams 3-chlorophenylhydrazine hydrochloride, and 200 ml. methanol was refluxed overnight. The reaction product mixture was washed up in the usual manner to yield 11 grams of crude 1-(3-chlorophenyl)-4-phenyl-3-pyrazolin-5-one. A sample recrystallized from methanol had a melting point of about 211°–212° C.

A mixture of 4 grams of the above prepared pyrazolinone, 20 ml. ethyl iodide, 20 ml. ethyl bromide, 3 grams potassium carbonate, and 40 ml. ethanol was refluxed for about 4 hours. The reaction product mixture was worked up to yield 0.9 grams of an oil which was identified as the desired product.

Calculated: C, 68.34; H, 5.06; N, 9.38; Found: C, 68.15; H, 4.89; N, 9.29.

EXAMPLE 12

2-Ethyl-4-phenyl-1-(α,α,α-trifluoro-3-tolyl)-3-pyrazolin-5-one

A mixture of 8.2 grams of the atropic acid, methyl ester, (prepared in Example 11), 8.5 grams 3-(trifluoromethyl)-phenyl-hydrazine hydrochloride, 100 ml. benzene and 4 grams triethylamine, was refluxed overnight and worked up to yield 6.5 grams of 4-phenyl-1-(α,α, α-trifluoro-3-tolyl)-3-pyrazolin-5-one having a melting point of about 210°–213° C.

A mixture of 2.2 grams of the pyrazolinone prepared above, 2 grams potassium carbonate, 25 ml. ethyl iodide and 25 ml. ethanol was refluxed for about 3 hours. The reaction mixture was worked up in the usual manner to yield an oil which was identified by NMR analysis as the desired product.

Other representative compounds of the present invention, synthesized in accordance with the foregoing teaching, include the following.

| Example No. | Compound Name | Melting Point |
| --- | --- | --- |
| 13 | 2-Methyl-1,4-diphenyl-3-pyrazolin-5-one | 170–173° C. |
| 14 | 2-Methyl-4-phenyl-1-(α,α,α-trifluoro-3-tolyl)-3-pyrazolin-5-one | 129–131° C. |
| 15 | 2-Methyl-4-phenyl-1-(3-chlorophenyl)-3-pyrazolin-5-one | 150–152° C. |
| 16 | 1-(4-Chlorophenyl)-2-methyl-4-(α,α,α-trifluoro-3-tolyl)-3-pyrazolin-5-one | 180–181° C. |
| 17 | 1-(3-bromophenyl)-2-methyl-4-(α,α,α-trifluoro-3-tolyl)-3-pyrazolin-5-one | 108–110° C. |
| 18 | 1-(3,4-dichlorophenyl)-2-ethyl-4-(α,α,α-trifluoro-3-tolyl)-3-pyrazolin-5-one | 120° C. |
| 19 | 1,4-Bis-(3-chlorophenyl)-2-methyl-3-pyrazolin-5-one | 145–147° C. |
| 20 | 1,4-Bis-(3-methoxyphenyl)-2-methyl-3-pyrazolin-5-one | 103–105° C. |
| 21 | 1,4-Bis-(3-methoxyphenyl)-2-ethyl-3-pyrazolin-5-one | 108–110° C. |
| 22 | 4-(2-chlorophenyl)-2-(3-chlorophenyl)-2-ethyl-3-pyrazolin-5-one | oil |

-continued

| Example No. | Compound Name | Melting Point |
|---|---|---|
| 23 | 1-(4-fluorophenyl)-2-methyl-4-(α,α,α-trifluoro-3-tolyl)-3-pyrazolin-5-one | 165° C. |
| 24 | 2-ethyl-1-(3-fluorophenyl)-4-(α,α,α-trifluoro-3-tolyl)-3-pyrazolin-5-one | 140–141° C. |
| 25 | 1-(2-chlorophenyl)-2-methyl-4-(α,α,α-trifluoro-3-tolyl)-3-pyrazolin-5-one | 175° C. |
| 26 | 2-Methyl-1-(3-tolyl)-4-(α,α,α-trifluoro-3-tolyl)-3-pyrazolin-5-one | 153–154° C. |
| 27 | 4-(3-chlorophenyl)-2-methyl-1-phenyl-3-pyrazolin-5-one | 149–150° C. |
| 28 | 1-phenyl-2-propyl-4-(α,α,α-trifluoro-3-tolyl)-3-pyrazolin-5-one | oil |
| 29 | 4-(3-fluorophenyl)-2-methyl-1-phenyl-3-pyrazolin-5-one | 134° C. |
| 30 | 2-ethyl-4-(4-fluorophenyl)-1-(α,α,α-trifluoro-3-tolyl)-3-pyrazolin-5-one | 126° C. |
| 31 | 1-(3-chlorophenyl)-2-ethyl-4-(2-(hydroxymethyl)phenyl)-3-pyrazolin-5-one | 147–152° C. |

The compounds described above have been tested in a number of algicidal test systems to determine the range of their aquatic algicidal efficacy. The results produced by the compounds in the representative tests reported below are exemplary of the activity of the compounds.

Compound application rates herein are expressed in part/million (ppm).

Blank spaces in the tables below indicate that the compound was not tested against the named species. In the tests below, observations 7 days after treatment for algicidal activity are recorded as to 1–5 injury rating visually:
1 = no effect
2 = slight effect
3 = moderate effect
4 = heavy effect
5 = 100% control Compounds are identified by their example numbers.

Aquatic Algicide Activity Test I

In this test *Chlorella pyrenoidosa*, *Scenedesmus obliquus*, and *Anacystis nidulans* were grown on Hughes' artificial media. Agar slants of each of these were used for inoculating the test media which was aqueous Hughes' media in all cases.

Compounds to be tested were formulated by pre-weighing 10 mg. in 12 ml. disposable glass vials to which 0.5 ml. acetone and 4.5 ml. of sterile 0.1% Tween 80 were added.

Suspensions of the various algal taxa were made by washing the agar slants with 5 ml. of sterile Hughes' media and pipetting the media into 400 ml. of sterile media. Using a sterilized automatic syringe, 2 ml. of the inoculated media were transferred to 12 ml. disposable glass vials for culturing. Testing at 10 ppm. was effected by adding 10 μl. of formulated compound to the culture vials which were then stoppered to avoid contamination. The treatments were usually twice replicated.

The results of Test I are set forth in Table I which follows. In the table, column 1 identifies the compounds by the number of the preparative example; column 2 lists the concentration of the test compound in the formulation; and columns 3–5 give the rating code at 7 days for the algal speciments against which the compounds were tested.

TABLE 1

| Example No. | Appln Rate ppm | Algal Control | | |
|---|---|---|---|---|
| | | Chlorella pyrenoidosa | Scenedesmus obliquus | Anacystis nidulans |
| 1 | 10 | 3 | 3 | 2 |
| 2 | 10 | 1 | 4 | 3 |
| 3 | 10 | 1 | 5 | 4 |
| 4 | 10 | 1 | 4 | 3 |
| 5 | 10 | 5 | 5 | 5 |
| 5 | 10 | 5 | 5 | 5 |
| 6 | 10 | 5 | 5 | 5 |
| 7 | 10 | 5 | 5 | 5 |
| 8 | 10 | 3 | 5 | 5 |
| 9 | 10 | 4 | 5 | 5 |
| 10 | 10 | 5 | 5 | 5 |
| 11 | 10 | 5 | 4 | 5 |
| 12 | 10 | 3 | 4 | 5 |
| 13 | 10 | 4 | 3 | 4 |
| 14 | 10 | 1 | 3 | 1 |
| 15 | 10 | 4 | 4 | 5 |
| 16 | 10 | 1 | 3 | 1 |
| 17 | 10 | 2 | 4 | 5 |
| 18 | 10 | 5 | 5 | 4 |
| 19 | 10 | 5 | 5 | 5 |
| 20 | 10 | 1 | 5 | 2 |
| 21 | 10 | 1 | 5 | 5 |
| 22 | 10 | 5 | 5 | 5 |
| 30 | 10 | 5 | 5 | 5 |
| 31 | 10 | 2 | 4 | 5 |
| 31 | 10 | 5 | 5 | 5 |

Aquatic Algicide Activity Test II

To further determine and better define the range of algicidal acticity, selected compounds were tested at concentrations of 1.0 ppm. and 0.5 ppm. The procedure was generally similar to that of Test I.

*Chlorella pyrenoidosa*, *Scenedesmus obliquus*, and *Anacystis nidulans* were grown on artificial media solidified with agar and transferred to aqueous media for the test period. The taxa were transferred to an aqueous media by using 5 ml. of sterile aqueous media to thoroughly wash and suspend the algal cells growing on the agar media. Hughes' media was used for all test species in this test. The 5 ml. suspension was added to 500 ml. of sterile media (one agar slant was used for each 500 ml. of nutrient media) and, using a sterilized automatic syringe, 10 ml. of inoculated media were added to each 30 ml. disposable tissue culture flask (Fulcon Plastics #3013).

Test compounds were weighed at 12 mg./12 ml. disposable vial and were formulated by adding 1 ml. acetone and 11 ml. 0.1% Tween 80 to yield a stock solution of 1 mg./ml. One ml. of this stock was added to another vial and then 9 ml. of sterile 0.1% Tween 80 were added. This solution was then pipetted into the alga culture flasks at 0.1 ml. and 0.05 ml. to obtain 1 ppm. and 0.5 ppm. respectively. Each concentration was replicated twice. The activity rating for this test was the same as that discussed above.

The results of Test II are set forth in the Table II which follows. In the table, column 1 identifies the compounds by number of the preparative example; column 2 lists the concentration of the test compound in the formulation; and columns 3–5 give the rating code at 7 days for the algal specimen against which the compounds were tested.

TABLE 2

| Example No. | Appln Rate ppm | Algal Control Chlorella pyrenoidosa | Scenedesmus obliquus | Anacystis nidulans |
|---|---|---|---|---|
| 3 | 1.0 | 1 | 5 | 5 |
|  | 0.5 | 1 | 5 | 4 |
| 5 | 1.0 | 5 | 5 | 5 |
|  | 0.5 | 5 | 5 | 5 |
| 5 | 1.0 | 5 | 5 | 4 |
|  | 0.5 | 4 | 5 | 4 |
| 6 | 1.0 | 4 | 5 | 4 |
|  | 0.5 | 4 | 5 | 4 |
| 7 | 1.0 | 5 | 5 | 5 |
|  | 0.5 | 5 | 5 | 5 |
| 9 | 1.0 | 5 | 5 | 5 |
|  | 0.5 | 5 | 5 | 5 |
| 10 | 1.0 | 5 | 5 | 5 |
|  | 0.5 | 4 | 5 | 5 |
| 11 | 1.0 | 1 | 5 | 4 |
|  | 0.5 | 1 | 5 | 4 |
| 11 | 1.0 | 3 | 5 | 4 |
|  | 0.5 | 1 | 5 | 3 |
| 15 | 1.0 | 1 | 4 | 2 |
|  | 0.5 | 1 | 3 | 2 |
| 17 | 1.0 | 1 | 5 | 5 |
|  | 0.5 | 1 | 5 | 3 |
| 18 | 1.0 | 5 | 5 | 4 |
|  | 0.5 | 3 | 5 | 2 |
| 19 | 1.0 | 5 | 5 | 5 |
|  | 0.5 | 5 | 5 | 4 |
| 19 | 1.0 | 2 | 5 | 5 |
|  | 0.5 | 1 | 5 | 2 |
| 22 | 1.0 | 3 | 5 | 4 |
|  | 0.5 | 3 | 5 | 4 |
| 30 | 1.0 | 1 | 3 | 1 |
|  | 0.5 | 2 | 1 | 3 |

Example 10 showed moderate to no activity when tested against different algal genera including *Chlamydomonas* and several species of *Anabena*.

Aquatic Algicide Activity Test III

This test was the same as Test II except that different algal taxa were used. The algae used in Test III included *Chlamydomonas moewusii, Anabaena flosaquae*, Anabaena sp. B-378, *Stichococcus bacillaris*, Anabaena sp. 1551, and Anabaena sp. 1552. *Stichococcus bacillaris* was grown on Hughes' media, *Anabaena flosaquae* on Bristol's media, and Anabaena sp. B-378, Anabaena sp. 1551, Anabaena sp. 1552, and *Chlamydomonas moewusii* were grown on Difco media. The inoculation, formulation, activity ratings, and all other procedures were the same as those described for Test II.

The results of Test III are set forth in Table III which follows. In the Table, column 1 identifies the compounds by number of the preparative example; column 2 lists the concentration of the test compound in the formulation; and columns 3–8 gives the rating code at 7 days for the algal specimen gainst which the compounds were tested.

TABLE 3

| Example No. | Appln Rate ppm | Algal Control Chlamydomonas moewsii | Anabaena flosaquae | Anabaena sp. B-378 | Stichococcus bacillaris | Anabaena sp. 1551 | Anabaena sp. 1552 |
|---|---|---|---|---|---|---|---|
| 5 | 1.0 | 3 | 1 | 1 | 5 | 1 | 1 |
|  | 0.5 | 5 | 1 | 4 | 5 | 1 | 1 |
| 6 | 1.0 | 5 | 1 | 3 | 3 | 1 | 3 |
|  | 0.5 | 3 | 1 | 5 | 3 | 1 | 1 |
| 7 | 1.0 | 5 | 1 | 1 | 3 | 1 | 2 |
|  | 0.5 | 3 | 1 | 5 | 4 | 1 | 1 |
| 9 | 1.0 | 2 | 1 | 1 | 5 | 1 | 3 |
|  | 0.5 | 3 | 1 | 3 | 5 | 1 | 4 |
| 10 | 1.0 | 4 | 1 | 3 | 2 | 1 | 1 |
|  | 0.5 | 5 | 1 | 1 | 5 | 1 | 2 |
| 19 | 1.0 | 5 | | 4 | 1 | 4 | 1 |
|  | 0.5 | 3 | | 1 | 1 | 1 | 1 |

The broad spectrum activity of the compounds of this invention is illustrated by the above examples. The test results point out the efficacy of the compounds against diverse algal taxa such that algologists and other plant scientists will recognize that the compounds of the present invention are broadly effective against a wide array of unwanted algae.

As the above test results demonstrate, the compounds are used to reduce the vigor of algae by contacting them with an algicidally-effective amount of one of the compounds. The term "reduce the vigor of" is used herein to refer to both killing and injuring the alga which is contacted with a compound. In some instances, as is clear from the test results, the whole population of the contacted alga is killed. In other instances, some of the algae in a population are killed and some are injured. It will be understood that reducing the vigor of the algae by injuring them is beneficial even though the algae initially survive the application of the compound. The algae, the vigor of which has been reduced, are unusually susceptible to the stresses which normally afflict algae, such as disease, temperature, mechanical injury due to the physical disruption of the water environmental medium, availability of nutrients, light, and so forth. Moreover injured algae shows retarded growth and reproductive failure.

Therefore the treated algae are likely to expire due to the stress of the environment, even though they initially survive application of the compound. Further, if the treated algae are growing in swimming pools, lakes, streams, reservoirs, natural or artificial ponds, or other aquatic environmental media which undergo physical disruption due to commercial or recreational use, the already susceptible algae are further injured and damaged by the stress. Still further, when the treated algae are growing in water supplies (including but not limited to swimming pools, lakes, streams, reservoirs, and natural or artificial ponds) which are desired to be free of aquatic algae, the reduction in their vigor necessarily tends to minimize the treated algae's odor, taste, appearance, physical presence, toxins, and other nuisances which the algae present.

The compounds of the present invention are particularly useful for reducing and elminating algal populations which present nuisances in swimming pools, lakes, streams, natural and artificial ponds, reservoirs, marinas, water works and supplies, fountains, animal water tanks and dispensers, pisciculture ponds, tanks, or holding areas, irrigation equipment and channels, and so forth.

The compounds are algicidally effective when applied to the aquatic algae directly or to the water medium with which the algae are in direct contact. The compounds of the present invention are effective against aquatic algae which are floating at the surface of the water medium, suspended beneath the surface, or are attached to a substrate beneath or at the surface of the water medium.

Accordingly, an important embodiment of this invention is a method of reducing the vigor of algae which comprises contacting the algae with an algicidally-effective amount of a compound of the invention. The term algicidally-effective amount refers to an amount which will reduce the vigor of the treated algae. In the context of this invention, algal spores, gametes, filamentous fragments or other reproductive structures which are contacted by application of the compounds to the water medium, are also regarded as algae.

Amounts of algicides are measured in parts/million or lbs/surface acre ft. and a specific amount, usually within a range of 0.01 ppm. to 100 ppm. or 0.0271 to 271 lbs/surface acre ft., is called an application rate. The best application rate of a given compound of the invention for the control of a given alga or combination of algae varies, depending upon the climate, the type of water medium to be treated, the organic content of the water medium, and other factors known to those of ordinary skill in algology, plant science, hydrology, or water quality control. It will be found however that the preferred application rate is usually in the range of about 0.1 ppm. to 10 ppm. or 0.271 to 27.1 lbs/surface acre ft.

It is not implied, of course, that all compounds of this invention are effective against all algae at all rates. Some compounds are more effective against some types of algae and other compounds are more effective against other types. It is within the ordinary skill of an algologist, plant scientist, hydrologist, or one skilled in water quality control to ascertain the algae which are most advantageously controlled with the various compounds, and the best application rate for the particular use.

The compounds are applied to the water medium and to the algae in the manner which is usual in algology, plant science, hydrology, or water quality control. While the procedure may be varied according to the specific conditions and application, it is best to apply the compounds in the form of algicidal formulations which may be water-dispersed.

Typical formulations of the compounds of the present invention include general emulsifable concentrates, wettable powders, granules, and the like. A general emulsifable concentrate could be comprised depending upon solubility, of up to 72% active compound (6 lbs/gal.), up to 85% surfactant, (such as ICI Atlox 3403 F/3404 F, Stephan's Toximul H/360B, or Tween 80), and a solvent such as xylene or orthochlorotoluene. A wettable powder formulation could be comprised of up to 90% active compound with the remainder lignin sulfonate, sodium lauryl sulfonate, silica, and inert clay. A granule formulation could be comprised of 0.1 to 90% active compound with the remainder granular clay.

The compounds of the present invention may also be used in controlled release formulations such as matrix systems, rubber strips, or mini-encapsulation. Moreover the compounds additionally have been found useful in water in oil or inverse emulsion systems such as the well known Visko Rhap (Rhodia) or Nalquatic (Nalco) systems which are commercially available and useful for site directed formulation. This type of formulation may be prepared with $CaCO_3$ to insure sinking the active compound to bottom dwelling algae, or pumped with air, to insure floating the compound if planktonic algae are being targeted.

Combining the compounds of the present invention with sodium alginate and calcium salts results in a formation which is highly viscous. Such a formulation is also site directed in that it is sticky and tends to adhere to the algae being treated.

It is understood that the compounds of the present invention may be formulated in many additional ways which are well known and recognized in the art.

It has become ordinary in algology, plant science, hydrology, water quality control, or aquatic management and chemistry to apply two or sometimes more chemicals simultaneously in order to control algae, aquatic plants, animals, and other pests with a single application of chemicals. The compounds of this invention lend themselves well to combination with other chemicals and may usefully be combined with aquatic plant herbicides, aquatic plant growth regulators, piscicides, molluscicides, insecticides, and others as may be desirable.

Stephan's Toximul H/360 B is a common surfactant well known in the art and available from the Stephan Chemical Company, Chicago, Ill. It is a sulfonate and nonionic blend.

Tween 80 is polysorbate 80 or polyoxyethylene (20) sorbitan monooleate.

ICI Atlox 3403F/3404F is a common emulsifier available from Atlas Chemical Industries, Inc., Chemical Division, Wilmington, Del., 19899. It is a nonionic and anionic blend.

Nalquatic is available from the Nalco Chemical Company, 6216 West 66th Place, Chicago, Ill., 60638. It is a polycarboxylate polymer.

Visko Rhap is available from Rhodia, P.O. Box 125, Monmouth Junction, N.J., 08852. It is a blend of water in oil emulsifier and solvents (U.S. Pat. No. 3,119,229).

We claim:

1. A method of reducing the vigor of algae which comprises contacting the algae with an algicidally effective amount of a compound of the formula

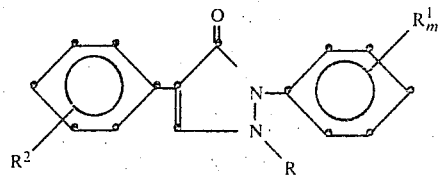

wherein

R represents $C_1$–$C_3$ alkyl;

$R^1$ and $R^2$ independently represent hydrogen, chloro, fluoro, bromo, methyl, methoxy, hydroxymethyl, or trifluoromethyl without restriction as to substituent or position except that when $R^1$ is para-chloro, m=1, and $R^2$ is simultaneously meta-trifluoromethyl, R is not simultaneously ethyl or propyl; and m=1 or 2 with the proviso that when m=2, $R^1$ is halo.

2. A method of claim 1 in which the algicidally effective compound is of the formula as recited in claim 1 wherein R represents $C_1$–$C_2$ alkyl;

$R^1$ represents bromo, chloro, fluoro, or trifluoromethyl, provided that $R^1$ is not para-chloro;

$R^2$ represents chloro or trifluoromethyl; and m=1–2.

3. A method of claim 2 wherein the amount of the algicidally effective compound is from about 0.1 ppm. to 10 ppm.

4. The method of claim 3 wherein the algicidally effective compound is 1-(3-chlorophenyl)-2-methyl-4-($\alpha,\alpha,\alpha$-trifluoro-3-tolyl)-3-pyrazolin-5-one.

5. The method of claim 3 wherein the algicidally effective compound is 1-(3-chlorophenyl)-2-ethyl-4-($\alpha,\alpha,\alpha$-trifluoro-3-tolyl)-3-pyrazolin-5-one.

6. The method of claim 3 wherein the algicidally effective compound is 1,4-bis-($\alpha,\alpha,\alpha$-trifluoro-3-tolyl)-2-ethyl-3-pyrazolin-5-one.

7. The method of claim 3 wherein the algicidally effective compound is 1-(3-bromophenyl)-2-ethyl-4-($\alpha,\alpha,\alpha$-trifluoro-3-tolyl)-3-pyrazolin-5-one.

8. The method of claim 3 wherein the algicidally effective compound is 2-ethyl-1-(4-fluorophenyl)-4-($\alpha,\alpha,\alpha$-trifluoro-3-tolyl)-3-pyrazolin-5-one.

9. The method of claim 3 wherein the algicidally effective compound is 1-(3-bromophenyl)-2-methyl-4-($\alpha,\alpha,\alpha$-trifluoro-3-tolyl)-3-pyrazolin-5-one.

10. The method of claim 3 wherein the algicidally effective compound is 1-(3-bromophenyl)-2-methyl-4-($\alpha,\alpha,\alpha$-trifluoro-3tolyl)-3-pyrazolin-5-one.

11. The method of claim 3 wherein the algicidally effective compound is 1-(3,4-dichlorophenyl)-2-ethyl-4-($\alpha,\alpha,\alpha$-trifluoro-3-tolyl)-3-pyrazolin-5-one.

12. The method of claim 3 wherein the algicidally effective compound is 1,4-bis-(3-chlorophenyl)-2-ethyl-3-pyrazolin-5-one.

13. The method of claim 3 wherein the algicidally effective compound is 4-(3-chlorophenyl-2-ethyl-1-($\alpha,\alpha,\alpha$-trifluoro-3-tolyl)-3-pyrazolin-5-one.

14. The method of claim 3 wherein the algicidally effective compound is 1,4-bis-(3-chlorophenyl)-2-methyl-3-pyrazolin-5-one.

15. The method of claim 3 wherein the algicidally effective compound is 4-(2-chlorophenyl)-1-(3-chlorophenyl)-2-ethyl-3-pyrazolin-5-one.

* * * * *